United States Patent [19]

Smith et al.

[11] 4,296,069

[45] Oct. 20, 1981

[54] APPARATUS FOR PROCESSING AN ANALYSIS SLIDE

[75] Inventors: Michael R. Smith; Anthony P. DiFulvio, both of Rochester, N.Y.

[73] Assignee: Eastman Kodak Company, Rochester, N.Y.

[21] Appl. No.: 159,562

[22] Filed: Jun. 16, 1980

[51] Int. Cl.³ .......................................... G01N 35/04
[52] U.S. Cl. .................................... 422/64; 119/35; 422/65
[58] Field of Search ...................... 23/230 R, 230 B; 422/64, 65, 66; 424/3; 353/113; 119/35, 39, 43; 435/809

[56] References Cited

U.S. PATENT DOCUMENTS

4,219,529 8/1980 Tersteeg et al. ...................... 422/64
4,224,033 9/1980 Glover et al. ........................ 422/64

Primary Examiner—Ronald Serwin
Attorney, Agent, or Firm—Donald D. Schaper

[57] ABSTRACT

Apparatus is provided for processing an analysis slide in a chemical analyzer which is particularly suitable for performing both endpoint and rate analyses. The slide-processing apparatus comprises a slide transfer mechanism for selectively transferring analysis slides between an incubator and a read station. The incubator includes a temperature-controlled chamber having a rotor disposed in a horizontal plane therein comprising slide-holding members adapted to support each of a plurality of analysis slides at individual stations. Each of the individual stations may be selectively positioned to a transfer location wherein the slide carried by the rotor is accessible for removal. The slide transfer mechanism accesses the slide at the transfer location, removes the slide from the incubator, and delivers the slide to the read station. Following analysis at the read station, the slide is returned by the slide transfer mechanism to the incubator if the slide is being employed for rate analysis. If the slide is being used for endpoint analysis, the slide is discarded through a diverter portion of the slide transfer mechanism.

6 Claims, 7 Drawing Figures

FIG. 7

APPARATUS FOR PROCESSING AN ANALYSIS SLIDE

CROSS-REFERENCE TO RELATED APPLICATIONS

Reference is made to commonly-assigned, copending U.S. Patent Applications: Ser. No. 857,344, entitled Method and Apparatus for Chemical Analysis, filed in the names of Clyde P. Glover et al., on Dec. 5, 1977, and now U.S. Pat. No. 4,224,032; Ser. No. 855,124, entitled Incubator for Chemical Analyzer, filed in the names of Glenn E. Tersteeg et al on Nov. 26, 1977, and now U.S. Pat. No. 4,219,529; Ser. No. 159,564, entitled Slide Distributor for a Chemical Analyzer, filed in the names of Montalto et al on even date herewith; and Ser. No. 159,550, entitled Incubator Including Cover Means for an Analysis Slide, filed in the names of Anthony P. DiFulvio et al on even date herewith.

BACKGROUND OF THE INVENTION

1. Field of the Invention

The invention relates to chemical apparatus for the automatic analysis of biological fluids, and more particularly, to apparatus for processing analysis slides including a slide transfer mechanism for transferring slides between an incubator and a read station.

2. State of the Prior Art

In recent years, a number of automated systems have been developed for carrying out quantitative chemical analyses of sample fluids. In the aforementioned U.S. Patent Application Ser. No. 855,124, there is described an incubator for use in a chemical analyzer, in which sample fluid is metered onto an analysis slide which is then transferred into an incubator. The incubator comprises a temperature-controlled chamber having a plurality of transfer locations wherein slides may be transferred into or out of the chamber; conveyor means rotatable in the chamber about a horizontal axis and having a plurality of slide-holding means for releasably holding the slides; and drive means for effecting movement of slides in the conveyor means within the chamber for positioning the slides for transfer at one of the transfer locations. Although slide transfer means are broadly mentioned in that application for moving the slides between the incubator and a read station of the analyzer, there is no suggestion of a slide transfer mechanism which can re-insert slides into the incubator to permit additional readings on the slide.

U.S. Pat. No. 3,574,064, to Binnings et al, discloses apparatus in which glass slides are fed from a single supply station onto a turntable. Slides carried on the turntable are moved past a metering station, and then through wash and incubation stations spaced around the periphery of the turntable. Slides processed by the apparatus are ejected from the turntable into a slide receiver adjacent the slide supply station. There is no provision for automatic analysis of the processed slides, and they must be manually removed from the slide receiver for examination under a laboratory microscope.

U.S. Pat. No. 2,904,914, to Trubert, discloses a lantern-slide carrier comprising a movable driver plate which is formed with a pair of flexible tongues. As the driver plate is manually reciprocated, one of the tongues moves a first slide from a magazine into a viewing position while the other tongue moves a second slide from the viewing position to a storage container. There is no suggestion that such a slide carrier could be used in clinical apparatus.

SUMMARY OF THE INVENTION

It is an object of the present invention to provide novel and improved apparatus for processing an analysis slide in a chemical analyzer which is particularly suitable for performing both rate and endpoint analyses.

The slide-processing apparatus comprises a slide transfer mechanism which selectively removes a slide from an incubator and transfers the slide to a read station which is adapted to measure a characteristic of a sample fluid. The slide is either returned to the incubator by the slide transfer mechanism for later analysis or is discarded by the slide transfer mechanism following analysis.

In accordance with a presently preferred embodiment of the invention, there is provided slide-processing apparatus for use in a chemical analyzer in which a sample fluid is metered onto a slide and is analyzed at a read station after an appropriate period of incubation. Conveyor means supports each of a plurality of slides in the incubator at individual stations and effects movement of the individual stations to a transfer location where the slides may be transferred from the incubator. A slide transfer mechanism is provided for transporting a slide from the transfer location to the read station wherein analysis of the slide occurs. Following such analysis, the slide is either returned by the slide transfer mechanism to the slide transfer location in the incubator, or the slide is discarded by a diverter portion of the slide transfer mechanism if no further readings on the slide are desired.

The invention is particularly suitable for use in apparatus adapted to perform analyses of blood sera in which the serum is dispensed onto a test element, or analysis slide, of the type which is formed as a multilayer element containing the necessary reagents for reaction with components of the serum. However, this invention is not limited to use with just such analysis slides, nor is it limited to just the analysis of blood sera, as other fluids can be used with apparatus of the type disclosed.

DESCRIPTION OF THE PREFERRED EMBODIMENT

In accordance with a presently preferred embodiment of the invention, slide-processing apparatus is provided for a chemical analyzer which performs analysis of a sample fluid deposited on an analysis slide. While the slide-processing apparatus described and claimed is particularly suited for the analyzer briefly disclosed herein and more fully described in the aforementioned U.S. Patent Application, entitled Slide Distribution for a Chemical Analyzer, it is also suitable for use with a chemical analyzer of the type shown and described in commonly-assigned U.S. Pat. No. 4,152,390, entitled Chemical Analyzer, issued in the names of Louis C. Nosco et al.

The invention is useful with analyzers in which the substrate which makes the test possible comprises a pair of electrodes selective to the ion activity of choice. Recent developments have provided the electrodes in essentially planar, dry form suitable for use in pairs in an analyzer. An example of such a test element is disclosed in Hamblen et al, U.S. Pat. No. 4,053,381, granted on Oct. 11, 1977. This patent describes a test element, or analysis slide, of the type which is used to potentiometrically designate the activity of ions in a liquid test solution.

The invention can also be used with other forms of test elements, as for example, the element disclosed in the commonly-owned patent to Przybylowitz et al, U.S. Pat. No. 3,992,158, granted on Nov. 16, 1976. The test element disclosed in this patent is formed as a multilayered element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular component present in the fluid.

Figure 1:
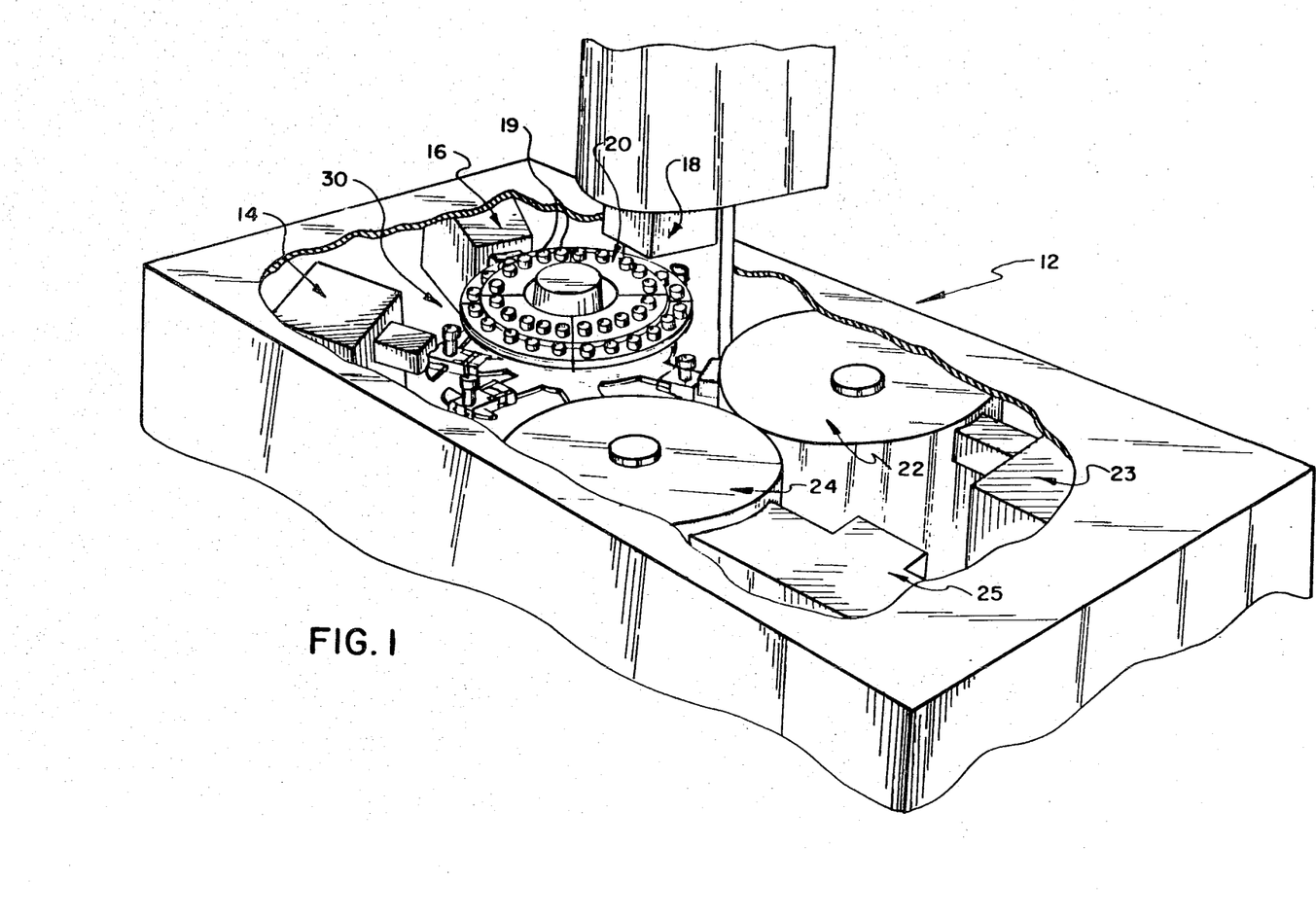
FIG. 1 is a perspective view of a chemical analyzer of the type which employs the slide-processing apparatus of the subject invention.

With reference to FIG. 1, there is shown analyzer apparatus 12 which comprises a housing 14 for a supply of analysis slides of the colorimetric type and a housing 16 for a supply of analysis slides of the potentiometric type. A metering device 18 is adapted to meter sample fluid from one of a plurality of cups 19 in a sample tray 20 onto an analysis slide in a slide distributor 30. A second metering device, not shown, works in conjunction with metering device 18 to also deposit reference fluid onto the analysis slides of the potentiometer type. After the metering operations, analysis slides of the potentiometric type are deposited in an incubator 22 from slide distributor 30, and analysis slides of the colorimetric type are deposited in an incubator 24. Incubators 22, 24, are adapted to cooperate respectively with read stations, or analysis means, 23, 25, for measuring a change in the analysis slides as a result of the fluid deposited thereon. A slide transfer mechanism, described below, is provided for moving the slides from the incubator 24 to the analysis means 25 and for returning or discarding the slides following analysis of the sample.

Figures 2, 4:
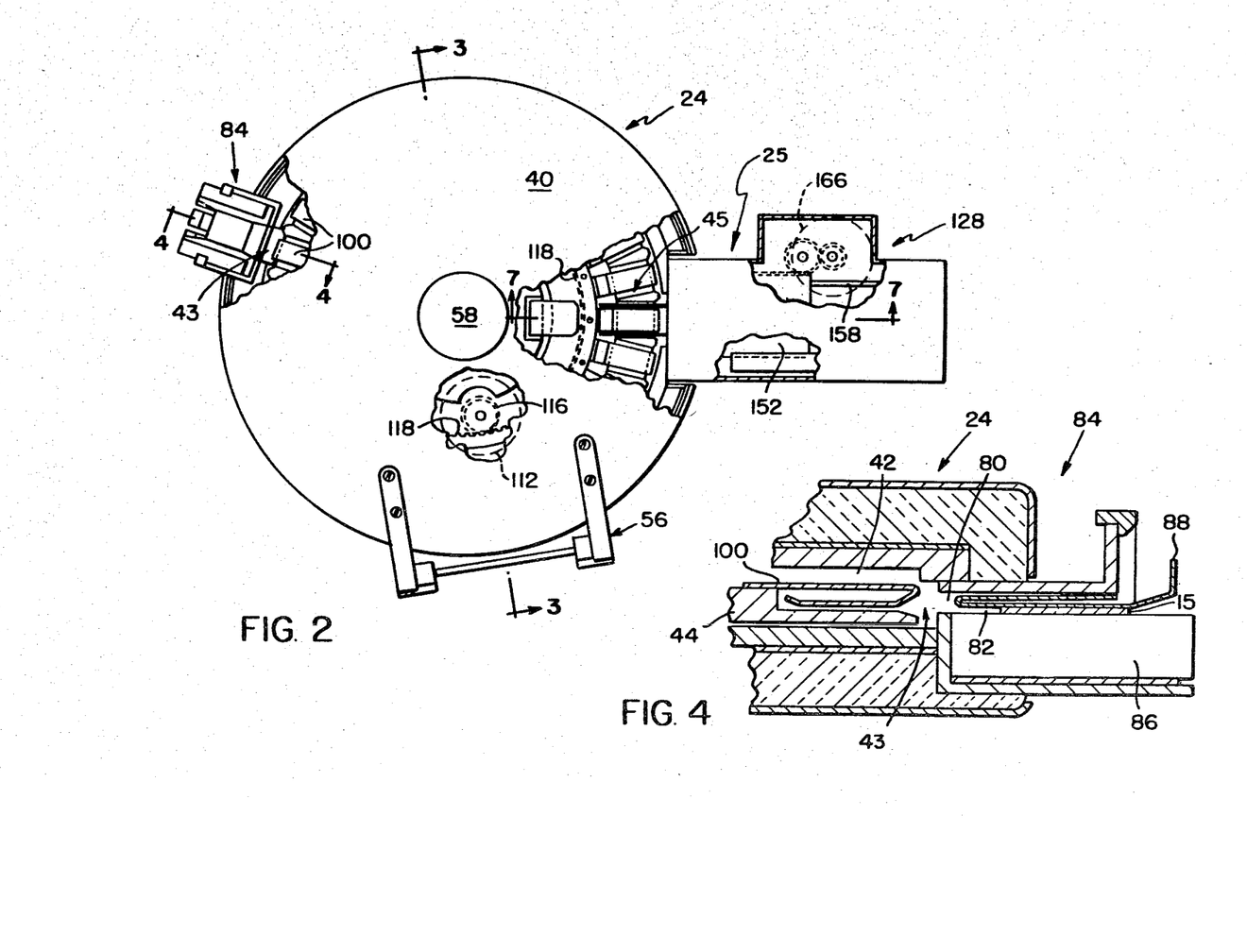
FIG. 2 is a top plan view of the slide-processing apparatus, with portions broken away to show elements of the apparatus.
FIG. 4 is a sectional view taken along line 4—4 in FIG. 2.
Figures 3, 5:
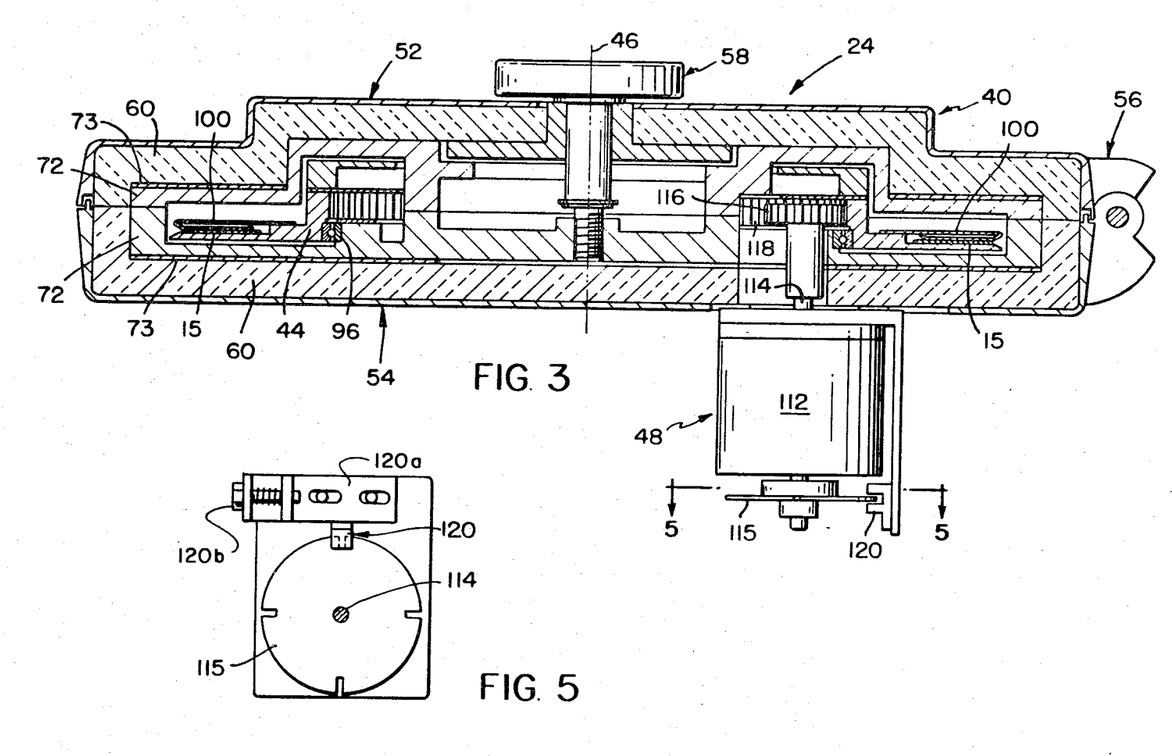
FIG. 3 is a sectional view taken along the line 3—3 in FIG. 2.
FIG. 5 is a sectional view taken along line 5—5 in FIG. 3.

In FIGS. 2 and 3 there is shown incubator 24 which comprises a housing 40 defining a generally cylindrical, temperature-controlled chamber 42, a circular slide conveyor or rotor 44 mounted for rotation within chamber 42 about a vertical axis designated 46, and a drive mechanism 48 for rotor 44. As will be described in greater detail hereinafter, rotor 44 is adapted to receive slides 15 at an input position 43, transport the slides in the chamber 42, and release and receive the slides at a transfer location 45. The housing 40 comprises a pair of mating sections 52, 54 which are pivotally joined by a hinge assembly 56. Section 52 may be pivoted from the closed position shown in FIG. 3, to an open or vertical position (not shown), to permit access to the chamber 42. In the closed position, section 52 may be secured in place by a threaded fastener assembly 58 which screws into section 54. Each of the sections 52, 54, preferably includes, at least in the area of the chamber 42, a double thickness of a suitable metal separated by a layer of insulation 60.

Heating elements 72, comprising aluminum heating blocks in contact with blanket heaters 73, are supported by sections 52, 54 at least proximate the outer portion of rotor 44. Preferably, the heating elements 72 are in physical contact with each other, at least along their peripheral areas, to provide heat transfer between the elements. Such heat transfer permits relatively accurate monitoring of the temperature of the heating elements 72 by means of a single thermistor (not shown) supported in contact with one of the elements.

Blanket heaters 73 for heating elements 72 may be of the type in which high-resistance wires are embedded in silicone rubber. Preferably, each blanket heater 73 includes two high-resistance wires which are independently controlled. During initial warmup, both wires of both blanket heaters 73 operate in a heating mode. Once a predetermined temperature is reached in the chamber 42, only one wire in each of the blanket heaters 73 is used to maintain the desired temperature.

The blanket heaters 73 are connected to a control circuit, not shown, which includes a thermistor for controlling the temperature of heating elements 72 through a conventional feedback arrangement. The control circuit regulates the blanket heaters for maintaining chamber 42 at a constant temperature, preferably 37° C. Other thermistors (not shown) may be positioned in the chamber 42 proximate the rotor 44 for purposes of calibration and determination of temperature variations throughout the chamber.

With reference to FIGS. 2 and 4, a load slot 80 is provided in housing 40 at an input position generally designated 43. Slot 80 is of a shape and size sufficient to allow the free passage of a slide 15 by shuttle mechanism (not shown) from the preheater assembly 84. Preheater assembly 84 is supported relative to housing 40 such that an exit opening 82 communicates with load slot 80 of incubator 30. Preheater 84 comprises an electrically-heated metal block 86 and a spring retainer 88 which is resiliently biased toward block 86. The spring retainer 88 holds a slide 15 in position in the preheater assembly until the shuttle mechanism moves the slide from the preheater into the incubator. Preferably, the portions of spring retainer 88 which contact with slide 15 are non-porous. This eliminates gas absorption from the slide and minimizes the carryover of reaction gases from slide to slide. Preheater 84 is adapted to raise the temperature of a slide 15 from ambient temperature to a temperature near the temperature maintained in the incubator chamber 42. Thus, a slide 15 entering chamber 42 does not materially affect the temperature therein, and a very precise temperature control can be maintained in the chamber.

Mounted for rotation within chamber 42 of housing 40 is rotor 44 for moving slides in a circular path about vertical axis 46. Rotor 44 is supported in incubator 22 by a ring bearing 96 (FIG. 3), and it is adapted to support each of a plurality of slides at individual slide-supporting positions or stations. In the preferred embodiment, the rotor holds up to 27 slides, and each slide is associried on rotor 44. The slide-holding means, comprising radially extending spring clips 100, are adapted to releasably hold a slide 15 against a portion of rotor 44 in an individual station. Clips 100 are preferably non-porous to eliminate gas absorption and minimize carryover of reaction gases. It will be apparent that clips 100 could also be integral with rotor 44.

With reference to FIGS. 2 and 3, there is shown a drive mechanism 48 which is provided to advance rotor 44 in precise increments and to hold the rotor in position during loading and unloading operations. Drive mechanism 48 comprises a 200 step per revolution stepper motor 112 having a shaft 114 which carries a gear 116 thereon. Gear 116 is adapted to drive a gear 118 which is integral with rotor 44. A preferred gear ratio of gear 116 to gear 118 is 6.75:1. As a result, one-fourth revolution of stepper motor 112 (50 steps) produces a 1/27th revolution of rotor 44 (one station advance). That is, one-fourth revolution of shaft 114 will advance rotor 44 sufficiently to move one station out of the transfer location 45 and the next station into the transfer location. This arrangement facilitates the precise positioning of slides 15 in the individual stations on rotor 44 relative to the input position 43 and the transfer location 45.

Referring now to FIGS. 3 and 5, positioning of the rotor 44 by the stepper motor 112 is controlled by an encoder disk 115 secured to shaft 114. Disk 115 has 4 equally spaced slots defined in a peripheral region. An optical sensing mechanism 120 is adapted to sense each of the slots in disk 115 as shaft 114 is rotatably driven by stepper motor 112. Through conventional circuitry (not shown) coupled to the optical sensing mechansim 120, the stepper motor 112 is advanced until the leading edge of a slot in the disk 115 is sensed plus one additional step. This places the middle of the slot at the sensor and a slide-supporting station of the rotor 44 at the desired position after each advancement of the rotor 44. As shown in FIG. 5, the optical sensing mechanism 120 includes a movable support 120a and an adjusting screw 120b. By appropriate positioning of the movable support 120a by screw 120b, the sensing mechanism 120 is calibrated such that the rotor 44 is stopped at the desired position after each advancement by stepper motor 112. It will also be apparent that by selecting appropriate control circuitry for motor 112, and gear ratios for gears 116 and 118, it is possible to provide other numbers of individual slide-supporting stations on rotor 44.

Figure 6:
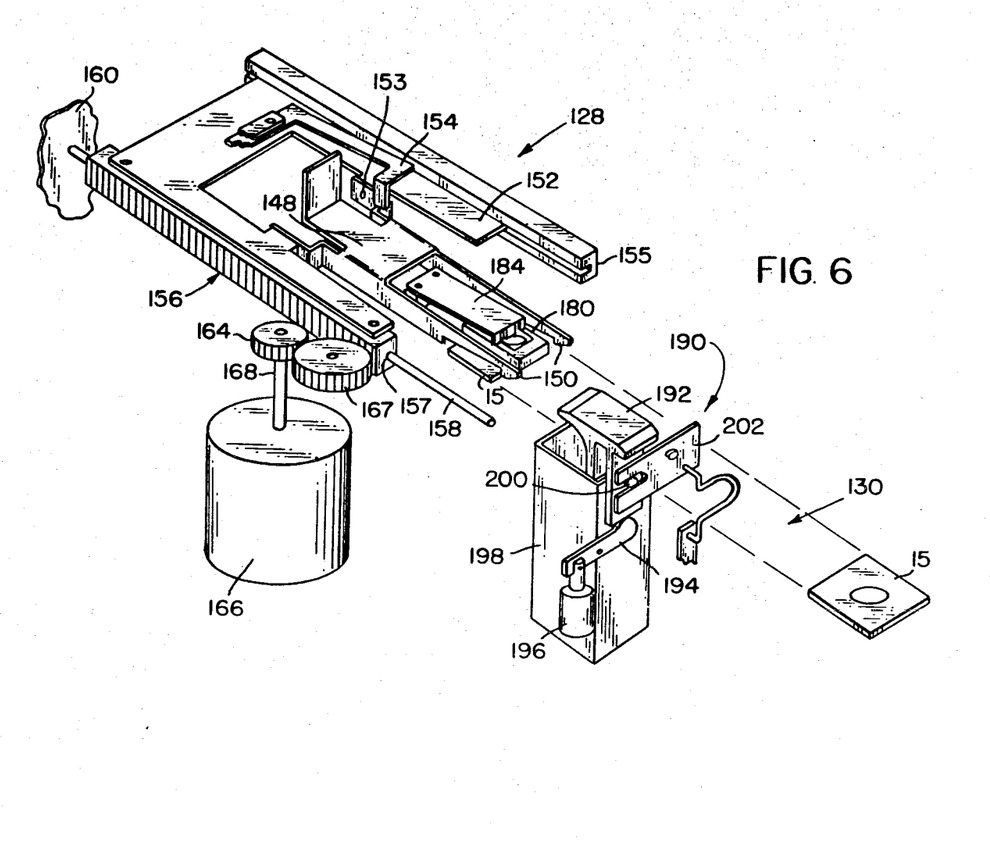
FIG. 6 is a perspective view of the slide transfer mechanism and showing the path of the analyses slides between the incubator and the read station.
Figure 7:
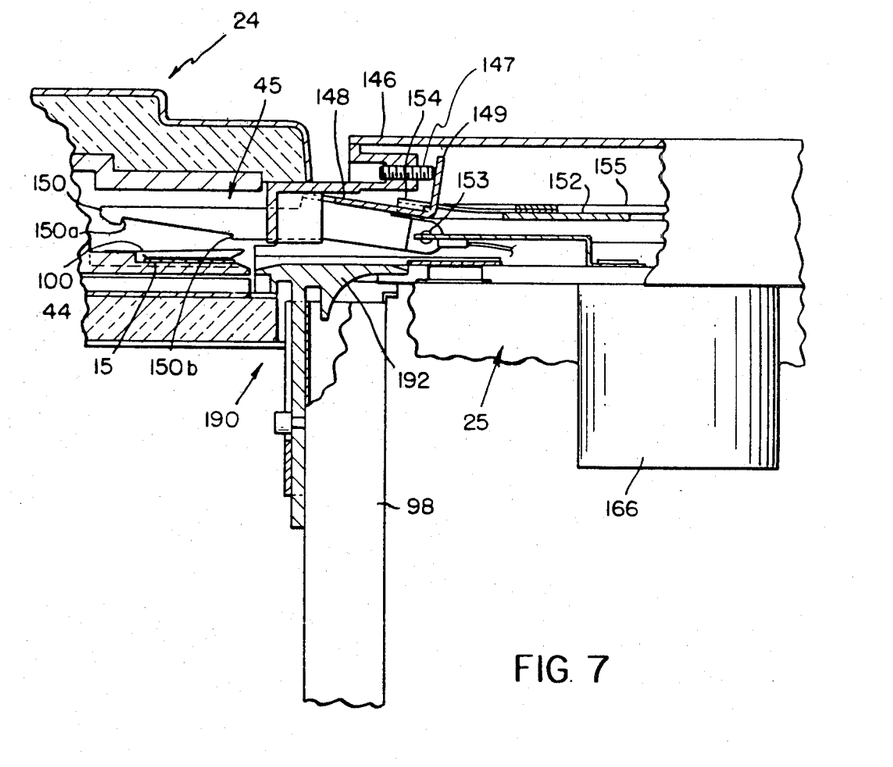
FIG. 7 is a sectional view of the slide transfer mechanism taken along line 7—7 in FIG. 2.

With reference to FIGS. 2, 6, and 7, a slide transfer means 128 comprises a housing 146 substantially enclosing a picker 148 having a bifurcated portion defining a pair of picker fingers 150. Each of the picker fingers 150 includes an undercut portion for receiving a slide 15. Front edges 150a and rear edges 150b of the undercut portion which are adapted to engage and move the slide 15 along a slide path between the transfer location 45 and the read station of the analysis means 25. The picker 148 is carried by a support plate 152 through a pair of hinge pins 153, one of which is shown. Preferably, picker 148 is biased to the position shown in FIG. 6 by a flat spring 154, partially shown, acting on the picker 148 near both of the hinge pins 153.

One side of the support plate 152 carries a rack 156. A guide member or rod 158, supported by the main transport housing 160 (FIG. 6), extends through a central opening 157 in rack 156. A first side of the support plate 152 is carried for axial movement along guide member 158. The other side of the support plate 152 is constrained to the direction of travel of the support plate by a slotted guide 155. The support plate 152 carrying picker 148 is adapted to be driven axially along the guide member 158 by a pinion 164 driving the rack 156 through an idler gear 167. Pinion 164 is driven in turn by a bi-directional stepper motor 166 through shaft 168 under the picker housing. If desired, the idler gear 167 may be placed between rack 156 and pinion 164 in an adjustable manner to remove backlash from the drive arrangement.

As shown partially in FIG. 7, and described in greater detail in the aforementioned U.S. Application Ser. No. 857,344, analysis means 25 is adapted to provide a reflectance reading of slides positioned at the read station. Analysis means 25 comprises a light source such as an incandescent bulb, a filter system, a lens system, a mirror which directs a beam of light against a slide 15 and a detection means.

In operation, a slide 15 is accessed in the slide transfer location 45 of the incubator 24 by the slide transfer mechansim 128 and then moved to the read station of analysis means 25. Slide transfer means 128 is initially positioned in a "home" position shown in FIG. 7, through movement of support plate 152 by the motor 112. In the "home" position, picker fingers 152 extend into the incubator 24 with the undercut portions generally extending over the slide transfer location 45 wherein a slide 15 may be positioned by rotor 44. A vertical tab 149 on the top of the picker 148 hits an adjustable stop 147 supported by the housing 146 and the picker fingers 150 are pivoted about hinge pins 153 against the bias of spring 154. A flag (not shown) on the support plate 152 interrupts an optical sensor (not shown) for detecting the transfer means 128 in the "home" position. Other known means may also be used for accurate positioning of the support plate 152.

To remove a slide from the incubator 24, the picker 148 is driven by the stepper motor 166 along the slide path 130 toward the read station of analysis means 25. The picker fingers 150 pivot over the slide 15 under the urging of spring 154 and the slide is engaged by edges 150a of the picker fingers. Edges 150a cooperate with the slide 15 to pull the slide out of the incubator 24 toward the read station. The step rate of stepper motor 166 is varied throughout the motion to allow accurate stopping and starting and provide quiet operation of the picker.

When slide 15 is positioned in the read station by the picker fingers 150, the slide is maintained in a desired position between a pressure pad 180 and a heated white reference block (not shown). A flat spring 184 urges the pressure pad against the slide 15 by the application of 4 to 6 oz. of force which is sufficient to maintain the slide in a predetermined reference plane for analysis. While in the read station, slide 15 remains under the undercut portion of the picker fingers 150.

Following analysis, the slide 15 is removed from the read station by the slide transfer mechanism 128 and either returned to the incubator 24 along the slide path 130 or diverted therefrom and discarded. If slide 15 is returned to the transfer location 45 by the slide transfer mechansim 128, it will be placed in a slide-supporting station of rotor 44 and maintained in the incubator 24 until the next reading in a rate analysis is to be performed. When it is time for the next reading, the slide would be indexed to transfer location 45 and again accessed by slide transfer mechanism 128. If endpoint analysis has been performed by analysis means 25, the slide 15 will be discarded. In either instance, after the slide 15 is read, the edges 150b of picker fingers 150 of the slide transfer mechanism engage the slide and cooperate to move the slide from the analysis means as the support plate 152 is driven in the reverse direction by stepper motor 166.

As shown in FIGS. 6 and 7, a disposal station 190 is positioned along the slide path 130. The disposal station 190 comprises a diverter 192 which is driven vertically through a link 194 by a pull-type solenoid 196. When slide 15 is being removed from or reloaded into a slide-supporting location of incubator 24 by the slide transfer mechanism 128, the solenoid 196 is not actuated and the slide 15 is moved by the slide transfer mechanism over the diverter 192. When slide 15 is to be discarded instead of being returned to the incubator 24, the solenoid 196 is actuated and the diverter 192 is raised. The slide 15 hits the curved bottom surface of the diverter and drops through a chute 198 into a disposal box (not shown).

Preferably, the diverter 192 has a pin 200 secured thereto and the pin 200 is captured by a spring-loaded member 202. In operation, engagement of pin 200 by spring-loaded member 202 returns the diverter 192 to a retracted position after the solenoid is deactuated.

The diverter 192 and the chute 198 can be removed for cleaning or clearing slide jams. When diverter 192 is removed, the spring-loaded member 202 is pivoted clockwise and the toggle action of the spring holds the member in this position until the diverter 192 is replaced. An optical sensor (not shown) may be included to sense the operative position of the diverter. In the preferred embodiment, if the slide 15 is to be discarded, the diverter 192 is commanded up before the picker fingers 150 move, and the slide 15 will drop through the chute 198. If the slide is to be reloaded into the incubator 24 the diverter is not commanded up. In either case, the picker fingers 150 are driven into the incubator 24 to the "home position" as previously described.

A control system for incubator 24, as well as for other functions of analyzer 12, could include a computer, not shown, which may take any of the various forms known in the art that include programmable minicomputers and programmable microprocessors. The instructions and method of programming such computers is well known in the art, and thus, no further explanation is considered necessary. In the use of such a computer, input data including sample identification, calibration values, and desired tests for each sample would be keyed into the computer. Output signals from the computer would be utilized to provide input signals to the analyzer components to control their operation at the appropriate time in the machine cycle. Results from analysis means 25 would be transmitted to the computer which would perform the necessary calculations, according to a stored program, to arrive at a concentration for a particular sample. The concentration would then be transmitted to a display or printout device.

The invention has been described in detail with particular reference to certain preferred embodiments thereof, but it will be understood that variations and modifications can be effected within the spirit and scope of the invention.

What is claimed is:

1. Apparatus for use in a chemical analyzer of the type which is adapted to measure a characteristic of a sample fluid deposited on an analysis slide, said apparatus comprising:

incubator means including a temperature-controlled chamber having a transfer location at which an analysis slide may be transferred into or out of said chamber and conveyor means for supporting a plurality of slides in said chamber and selectively moving each of the analysis slides to and from said transfer location;

means defining a read station wherein said characteristic can be measured; and slide transfer means for moving an analysis slide along a slide path extending between said incubator means and said read station, said slide transfer means including diverter means selectively conditionable in (1) a first condition wherein an analysis slide can be freely moved by said slide transfer means along said slide path and (2) a second condition wherein an analysis a slide being moved along said slide path by said slide transfer means is diverted from said slide path.

2. Apparatus for use in a chemical analyzer of the type which is adapted to perform endpoint and rate analyses in measuring a characteristic of a sample fluid deposited on an analysis slide, said apparatus comprising:

incubator means including (1) a housing defining a temperature-controlled chamber and a transfer location wherein an analysis slide may be transferred into or out of said chamber and (2) conveyor means horizontally disposed within said chamber, said conveyor means including a plurality of individual locations each of which is adapted to receive and support an analysis slide in a horizontal position for movement to and from the transfer location;

means defining a read station wherein endpoint and rate analyses may be performed to determine a characteristic of a sample fluid on an analysis slide; and slide transfer means including transport means for moving an analysis slide along a slide path extending between said transfer location and said read station.

3. Apparatus as set forth in claim 2 wherein said slide transfer means further includes diverter means selectively conditionable in (1) a first condition in which an analysis slide can be moved by said transport means along said slide path between said transfer location and said read station and (2) a second condition in which an analysis slide being moved along said slide path by said transport means from said read station toward said transfer location is diverted from said slide path by said diverter means.

4. Apparatus as set forth in claim 2 wherein said slide transfer means further includes diverter means selectively positionable transverse said slide path for diverting an analysis slide from the slide path as the analysis slide is being moved along said slide path by said transport means.

5. In a chemical analyzer having a metering station for depositing a sample fluid on an analysis slide, an incubator including a conveyor for supporting the analysis slide, means for moving the analysis slide from the metering station to the conveyor, and analysis means for performing endpoint and rate analyses in measuring a characteristic of the sample fluid on said slide, the improvement which comprises:

means for transporting the analysis slide between the incubator and the analysis means; and means for selectively diverting an analysis slide being transported from the analysis means toward the incubator and for discarding the analysis slide.

6. Apparatus for use in a chemical analyzer in which a sample fluid is metered onto a generally planar slide which is analyzed after an appropriate period of incubation, said apparatus comprising:

housing means defining a temperature-controlled chamber, said housing means being formed from a pair of sections, one of said sections being movable relative to the other to permit access to said chamber;

rotor means in said chamber, said rotor means being disposed in a generally horizontal plane and including a peripheral portion for receiving and supporting slides thereon in a horizontal position, said rotor means having a plurality of slide holding means extending radially over said portion for releasably holding slides supported thereon;

drive means for said rotor means, said drive means being adapted to effect movement of the slides in the rotor means within said chamber and to stop said rotor means in a position such that slides can be transferred into or out of said chamber; and slide transfer means for moving slides into and out of said chamber.

* * * * *